(12) United States Patent
Indermuhle et al.

(10) Patent No.: US 7,615,190 B2
(45) Date of Patent: Nov. 10, 2009

(54) MICRODEVICE AND METHOD FOR DETECTING A CHARACTERISTIC OF A FLUID

(75) Inventors: Pierre F. Indermuhle, Hayward, CA (US); Peter Wagner, Belmont, CA (US)

(73) Assignee: Zyomyx, Inc., Hayward, CA (US)

( * ) Notice: Subject to any disclaimer, the term of this patent is extended or adjusted under 35 U.S.C. 154(b) by 811 days.

(21) Appl. No.: 10/829,021

(22) Filed: Apr. 20, 2004

(65) Prior Publication Data

US 2004/0197931 A1 Oct. 7, 2004

Related U.S. Application Data

(60) Division of application No. 09/759,106, filed on Jan. 11, 2001, now Pat. No. 6,794,197, which is a continuation-in-part of application No. 09/353,554, filed on Jul. 14, 1999, now Pat. No. 6,596,545, which is a continuation-in-part of application No. 09/115,397, filed on Jul. 14, 1998, now Pat. No. 6,576,478.

(60) Provisional application No. 60/175,997, filed on Jan. 12, 2000.

(51) Int. Cl.
*C12Q 1/68* (2006.01)
*G01N 15/06* (2006.01)
*G01N 27/00* (2006.01)
*G01N 21/00* (2006.01)
*G01N 21/66* (2006.01)
*B01L 3/02* (2006.01)
*B01L 11/00* (2006.01)

(52) U.S. Cl. .......................... 422/58; 422/50; 422/68.1; 422/82.01; 422/82.02; 422/82.03; 422/82.05; 422/82.08; 422/100; 422/103

(58) Field of Classification Search ...................... None
See application file for complete search history.

(56) References Cited

U.S. PATENT DOCUMENTS

| 4,894,146 A | 1/1990 | Giddings |
| 5,304,487 A | 4/1994 | Wilding et al. |

(Continued)

FOREIGN PATENT DOCUMENTS

WO   WO 96/04547   2/1996

(Continued)

OTHER PUBLICATIONS

Andreas Manz, et al., "Planar chips technology for miniaturization and integration of separation techniques into monitoring systems—Capillary electrophoresis on a chip", Journal of Chromatography, 1992, 253-258, No. 593, Elsevier Science Publishers B.V., Amsterdam.

(Continued)

*Primary Examiner*—Jill Warden
*Assistant Examiner*—Timothy G Kingan
(74) *Attorney, Agent, or Firm*—Townsend and Townsend and Crew LLP

(57) ABSTRACT

A microdevice for supporting a flowing fluid is disclosed. In one embodiment, the microdevice includes a substrate and a pair of generally parallel, spaced wall members on the substrate. At least one of the wall members includes a pair of structures defining an opening.

19 Claims, 13 Drawing Sheets

U.S. PATENT DOCUMENTS

| | | | |
|---|---|---|---|
| 5,376,252 A | 12/1994 | Ekstrom et al. | |
| 5,635,358 A | 6/1997 | Wilding et al. | |
| 5,653,864 A | 8/1997 | Gotoh et al. | |
| 5,674,698 A | 10/1997 | Zarling et al. | |
| 5,716,825 A | 2/1998 | Hancock et al. | |
| 5,726,026 A | 3/1998 | Wilding et al. | |
| 5,849,208 A | 12/1998 | Hayes et al. | |
| 5,854,684 A | 12/1998 | Stabile et al. | |
| 5,872,010 A | 2/1999 | Karger et al. | |
| 5,942,443 A | 8/1999 | Parce et al. | |
| 6,068,752 A | 5/2000 | Dubrow et al. | |
| 6,074,725 A * | 6/2000 | Kennedy | 428/188 |
| 6,083,763 A | 7/2000 | Balch | |
| 6,107,080 A | 8/2000 | Lennox | |
| 6,132,685 A | 10/2000 | Kercso et al. | |
| 6,150,180 A | 11/2000 | Parce et al. | |
| 6,153,073 A | 11/2000 | Dubrow et al. | |
| 6,159,739 A * | 12/2000 | Weigl et al. | 436/52 |
| 6,171,850 B1 | 1/2001 | Nagle et al. | |
| 6,171,865 B1 * | 1/2001 | Weigl et al. | 436/52 |
| 6,368,871 B1 | 4/2002 | Christel et al. | |
| 6,524,790 B1 * | 2/2003 | Kopf-Sill et al. | 435/6 |
| 6,794,197 B1 | 9/2004 | Indermuhle et al. | |

FOREIGN PATENT DOCUMENTS

| | | |
|---|---|---|
| WO | WO 00/04390 | 1/2000 |

OTHER PUBLICATIONS

Adam T. Woolley, et al., "Ultra-high-speed DNA fragment separations using micofabricated capillary array electrophoresis chips", Proc. Natl. Acad. Sci. USA, Nov. 1994, pp. 11348-11352, vol. 91.

Motoi Nakao, et al., "High-resolution pH imaging sensor for microscopic observation of microorganisms", Sensors and Actuators B 34, Apr. 24, 1996, pp. 234-239.

Yoshitaka Ito, "High-spatial resolution LAPS", Sensors and Actuators B 52, May 20, 1998, pp. 107-111.

S. R. Manalis, et al., "Microvolume field-effect pH sensor for the scanning probe microscope", Applied Physics Letters, Feb. 21, 2000, pp. 1072-1074, vol. 76, No. 8.

* cited by examiner

MICRODEVICE AND METHOD FOR DETECTING A CHARACTERISTIC OF A FLUID

CROSS REFERENCE TO RELATED APPLICATIONS

This application is a divisional of U.S. patent application Ser. No. 09/759,106, filed Jan. 11, 2001 now U.S. Pat. No. 6,794,197, which is a continuation-in-part of U.S. patent application Ser. No. 09/353,554, filed Jul. 14, 1999 now U.S. Pat. No. 6,596,545, which is a continuation-in-part of U.S. patent application Ser. No. 09/115,397, filed Jul. 14, 1998 now U.S. Pat. No. 6,576,478. This application also claims the benefit of the filing date of U.S. provisional patent application No. 60/175,997, filed Jan. 12, 2000. All of the above U.S. provisional and non-provisional applications are assigned to the same assignee and are all herein incorporated by reference in their entirety for all purposes.

BACKGROUND OF THE INVENTION

Work is now underway to develop microfluidic devices for analyzing chemical or biological fluids. A "microfluidic" device typically includes fluid channels having microscale dimensions. For example, a fluid channel in a typical microfluidic device may have a width of less than about 1000 microns.

In a typical application for a microfluidic device, a fluid containing a chemical compound may flow towards a reaction site on the microfluidic device. At the reaction site, the fluid may contact another fluid containing a different substance. The characteristics of the resulting fluid passing downstream of the reaction site may be detected to determine if the chemical compound reacts with the substance. The characteristics of the fluid may correspond to, for example, the concentration of the chemical compound in the fluid stream. If the concentration of the chemical compound in the fluid passing downstream of the reaction site is lower than the concentration of the chemical compound upstream of the reaction site, then it is likely that the chemical compound reacts with the substance.

Microfluidic analytical systems have a number of advantages over other types of analytical systems. For example, microfluidic systems are particularly well suited for analyzing or reacting samples with low volumes. In a typical microfluidic system, samples on the order of nanoliters or even picoliters can be reacted or analyzed. Because of the small volumes of fluids being handled, microfluidic analytical systems may be used to rapidly assay large numbers of samples. The assays can be performed to study the effect of numerous compounds in various biological processes. For example, test compounds that may block, reduce, or enhance the interactions between different biological molecules, such as a receptor molecule and a corresponding ligand, may be identified as potential candidate drugs.

In recent years, the number of test compounds produced by modern combinatorial chemistry techniques has dramatically increased. While conventional microfluidic systems can be used to test the increasing number of compounds, the throughput of such systems could be improved. There is a continuing need to screen large numbers of samples quickly and accurately.

Embodiments of the invention address this and other problems.

SUMMARY OF THE INVENTION

Embodiments of the invention can be used to quickly detect the characteristics of fluids in a microdevice. Embodiments of the invention can be used for, for example, high-throughput drug candidate screening and medical diagnostics.

One embodiment of the invention is directed to a microdevice for supporting a flowing fluid. The microdevice comprises: a substrate; and a pair of generally parallel, spaced wall members on the substrate, wherein at least one of the wall members includes a pair of structures defining an opening.

Another embodiment of the invention may be directed to a microdevice comprising: a substrate; a plurality of wall members; and a plurality of fluid channels, wherein each of the fluid channels is defined by adjacent wall members in the plurality of wall members, wherein each wall member comprises an opening that is formed by opposed beveled structures of the wall member and that communicates the adjacent fluid channels.

Another embodiment of the invention is directed to a method for detecting a characteristic of a fluid, the method comprising: (a) inserting a probe into a fluid channel in a microdevice; (b) detecting a characteristic of a first fluid flowing in the first fluid channel; (c) moving the probe from the first fluid channel through an opening in one of the walls defining the first fluid channel and to a second fluid channel adjacent to the first fluid channel; and (d) detecting a characteristic of a second fluid flowing through the second fluid channel.

Another embodiment of the invention is directed to an analytical assembly comprising: a detection assembly comprising a plurality of detection devices; and a microdevice comprising a plurality of wall members and a plurality of fluid channels, wherein each of the fluid channels is defined by adjacent wall members in the plurality of wall members.

Another embodiment of the invention is directed to a method for detecting a characteristic of a fluid, the method comprising: flowing a plurality of different fluids through respective fluid channels in a microdevice, each of the fluid channels in the microdevice being formed by adjacent pairs of wall members; and detecting characteristics of the plurality of different fluids substantially simultaneously using a plurality of detection devices as the different fluids flow through their respective fluid channels.

These and other embodiments of the invention are described in further detail with reference to the Figures and the Detailed Description.

DETAILED DESCRIPTION

Figure 1:
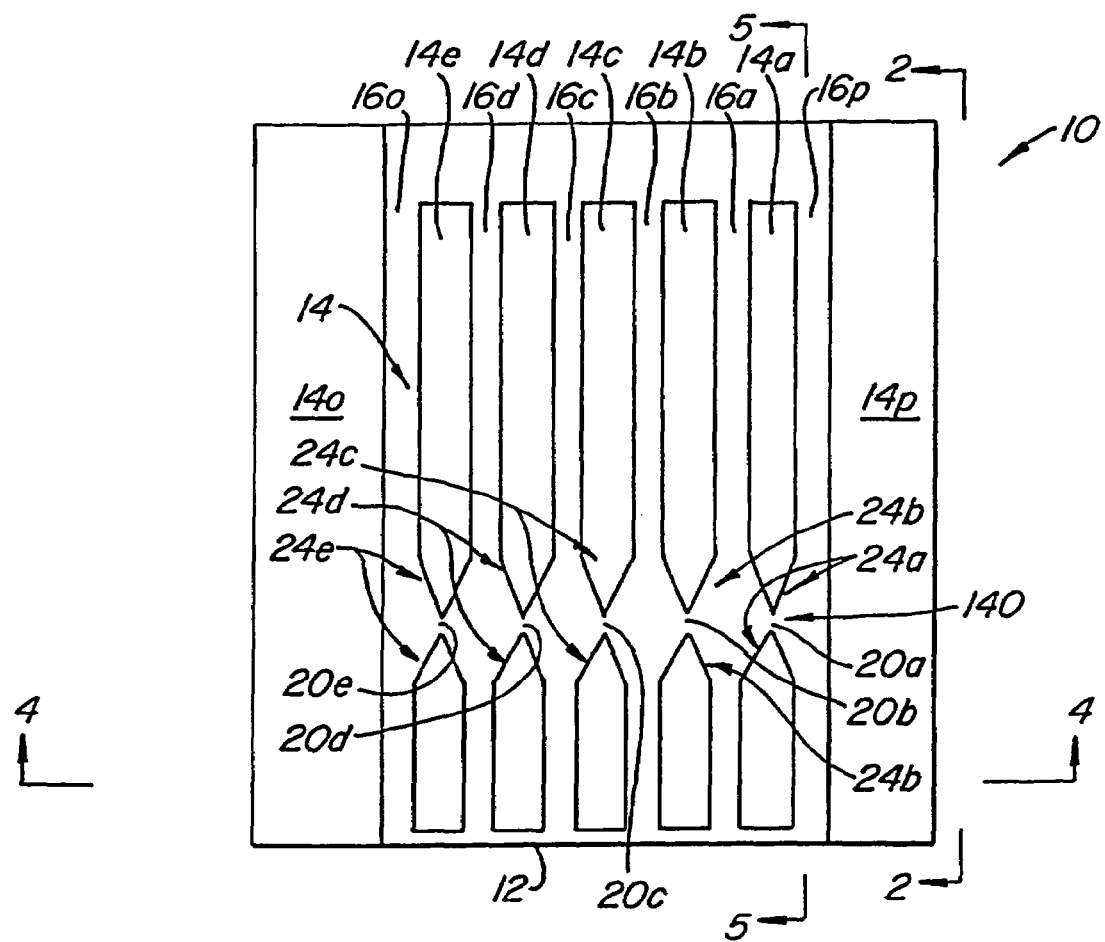
FIG. 1 shows a top view of a microdevice according to an embodiment of the invention.

Embodiments of the invention can be used to rapidly detect characteristics of a plurality of different fluids. The fluids may be gases or liquids. Exemplary liquids include biological fluids such as blood or urine, cell extracts, organic fluids, solvents, aqueous solutions, and the like. Exemplary gases include air samples, hydrocarbon gases, etc. Regardless of the form of the fluids, the fluids may comprise atoms, organic or inorganic molecules such as proteins, organelles such as cells, and the like.

The different fluids flow through a plurality of different fluid channels at a detection region of a microdevice. The different fluids may have distinct characteristics and may be the products of events that occur before the different fluids flow through the detection region of the microdevice. For example, the different fluids may be downstream products of upstream events such as potential or actual interactions between substances. Events may include chemical or biological reactions between two substances and binding events between two substances.

Downstream of the events, characteristics of the fluids can be detected at the detection region of the microdevice. The characteristics of the fluids that are detectable may be either quantitative or qualitative in nature. In some embodiments, characteristics of the fluids such as emitted radiation (e.g., light), conductivity, the pH and the like of the different fluids flowing in the different fluid channels can be detected to analyze the different fluids. Such characteristics may correspond to the types and/or amount of substances in the fluids. In some embodiments, the detected characteristics may serve as a direct or an indirect indicator of the concentration or amount of a particular substance in the fluid. For example, solutions containing protons are conductive. The conductivity or resistance of a fluid may be an indirect indicator of the concentration of protons in the fluid.

Interactions that can be assayed according to embodiments of the invention may be any type of interaction normally observed for biological moieties including, for example, a catalytic reaction of an enzyme, a binding event, or a translocation by a membrane protein through a lipid bilayer. In embodiments of the invention, separate fluid samples can be screened for their ability to interact with a biological moiety. For example, different fluid samples containing respectively different substances can flow through separate fluid channels in a microdevice and can be delivered to separate reaction sites on the microdevice. Each of the reaction sites may comprise an immobilized biological moiety, and the immobilized moieties may be bound to respective surfaces of different fluid channels. At the reaction sites, the biological moieties may or may not interact with the different fluid samples. Downstream of the reaction sites, the characteristics of the different fluids may be detected, either directly or indirectly to determine if any of the fluids of the substances in the different fluids have interacted (e.g., by binding together) with the immobilized biological moiety at each reactive site. For example, one or more detection devices downstream of the reactive sites may measure the concentration of the different substances in the fluids passing downstream of the reaction sites by detecting characteristics of the fluids. If the concentration of a substance in a fluid passing downstream of a reaction site is less than the concentration of the substance in a fluid upstream of the reaction site, then it is likely that the substance in the fluid is interacting (e.g., binding or reacting) with the immobilized biological moiety. On the other hand, if the concentration of a substance in a fluid downstream of the reaction site is substantially equal to the concentration of the substance upstream of the reaction site, then it is likely that little or no interaction is occurring between the substance in the fluid and the immobilized biological moiety.

In another example, upstream events may be specific conditions that are applied to different fluids in the different fluid channels to see if the fluids or substances in the fluids change as a result of the conditions. For instance, a plurality of different fluids may be subjected to different heating, cooling, and irradiation (e.g., with light) conditions. Characteristics in the fluids passing downstream of these events may be detected to determine if the conditions affect the fluids.

In some embodiments of the invention, characteristics of the different fluids in the fluid channels may be detected by using a probe. The probe may pass through a plurality of different fluids in respective fluid channels by passing through openings in wall members that define the fluid channels. The characteristics of the fluids in these fluid channels can be quickly detected without exposing the end of the probe to an environment outside of the flowing fluid.

In other embodiments of the invention, a plurality of detectors may detect characteristics of a plurality of fluids flowing through a plurality of fluid channels in a microdevice substantially simultaneously. A detection assembly comprising multiple detectors may be used to detect the characteristics of the fluids flowing in the fluid channels substantially simultaneously. In these embodiments, the wall members defining the plurality of fluid channels may or may not have openings.

These and other embodiments are described in further detail below.

I. Embodiments Using Microdevices

One embodiment of the invention is directed to a microdevice. The microdevice may include a plurality of fluid channels defined by a plurality of wall members. The plurality of wall members may include at least one wall member having at least one opening that communicates two adjacent fluid channels. An opening in the wall member may be formed by opposing beveled structures at the internal ends of portions of the wall member. In embodiments of the invention, different fluids flowing in the adjacent fluid channels may have a laminar profile and do not mix in an appreciable manner as they flow past the opening and contact each other at the opening. Intermixing between the contacting fluids is minimal, even though there is no physical barrier in the wall member at the opening.

When openings in the respective wall members in the microdevice are aligned, a slot may be formed by the aligned openings. A probe disposed in a fluid in a fluid channel can move laterally through the slot and from fluid channel to fluid channel. For example, the probe can contact a fluid in a fluid channel and can detect a characteristic of that fluid. The probe can then pass through an opening in a wall member defining the fluid channel to an adjacent fluid channel where a characteristic in the adjacent fluid channel may be detected. By analyzing different fluids in this manner, characteristics of the different fluids in the fluid channels can be quickly and accurately detected by the probe and subsequently analyzed. For example, in some embodiments, the characteristics of ten different fluids flowing in the different fluid channels may be accurately detected in less than one minute.

Illustratively, a probe for a pH sensor may be placed in a fluid channel to detect the pH of the fluid in that channel. Then, the probe can move laterally from one fluid channel to another adjacent fluid channel through the opening in a wall member disposed between these two fluid channels. The lateral movement of the probe can take place without withdrawing the probe from the fluids. Once the probe is in contact with the fluid in the adjacent channel, the pH of the fluid in the adjacent channel can be detected. This process can be repeated as the probe moves through the slot formed by the aligned openings in the wall members.

Embodiments of the invention provide a number of advantages. For example, in embodiments of the invention, a probe can pass through a number of fluid channels and can detect characteristics of the fluids in the fluid channels quickly and accurately. The probe need not be withdrawn from the fluid flowing in a channel and then inserted into an adjacent fluid channel. The distance that the probe travels between adjacent fluid channels is minimized thus reducing the time needed to analyze the fluids flowing in the microdevice. Moreover, since a probe need not be withdrawn from a fluid, the probe need not be aligned in a z-direction (i.e., relative to a x-y plane formed by the orientation of the microdevice) as it moves from fluid channel to fluid channel. The z-direction alignment step takes time and increases the chance of damaging the probe. For example, if a probe is inserted too far into a fluid channel, the probe may contact the fluid channel bottom surface potentially damaging the probe. In embodiments of the invention, the probe can be aligned in the z-direction once. To detect the characteristics of other fluid streams, the probe may move in an x- or y- direction while remaining a predetermined distance above the fluid channel bottoms. Also, by keeping the probe at a substantially constant z position, the reliability of measurements conducted by the probe can be improved in some instances. For example, the characteristics of a fluid flowing in a fluid channel may be a function of insertion depth in a fluid. Keeping a probe at a substantially constant z position when detecting characteristics of multiple fluids can eliminate any potential variation in any detected characteristics that may be due to different probe insertion depths. Furthermore, in embodiments of the invention, purging is not required between two successive detections (e.g., two successive measurements). In some conventional microfluidic devices, different fluids to be analyzed pass through a single fluid channel. Purging fluids are needed to separate the different fluids as they flow in series through the fluid channel. However, in embodiments of the invention, different fluids may flow in different, parallel fluid channels at a detection region in the microdevice. The fluids in the different fluid channels may be detected in series or in parallel without using purging fluids. Furthermore, the microdevice embodiments of the invention are especially suitable for use with biosensors. Typical biosensors may contain biological molecules such as lipids, enzymes, or receptors. If biological molecules such as these are exposed to air, they may become inactive. Moreover, a typical biosensor may have a variable "wetting" period after a sample fluid is applied to the biosensor. In embodiments of the invention, a probe can pass between different fluid streams without exposing the probe to an external environment such as air. Accordingly, the microdevice embodiments of the invention are especially useful for containing fluids that are to be analyzed using a biosensor. In addition, since fluid streams can contact each other yet not mix in an appreciable manner in embodiments of the invention, reactions at the interface of two flowing fluids may be analyzed. One or more probes may detect the characteristics of a fluid passing downstream of the interface of the two flowing fluids to study the interaction between the two fluids.

A microdevice embodiment is shown in FIG. 1. FIG. 1 shows a microdevice 10 comprising a substrate 12, a plurality of inner wall members 14a-14e, and a plurality of outer wall members 14o, 14p. The plurality of inner wall members 14a-14e is disposed between the outer wall members 14o, 14p. Both the inner wall members 14a-14e and the outer wall members 14o, 14p are disposed on the substrate 12. In this example, the inner wall members 14a-14e and the outer wall members 14o, 14p are substantially parallel to each other.

Figure 2:
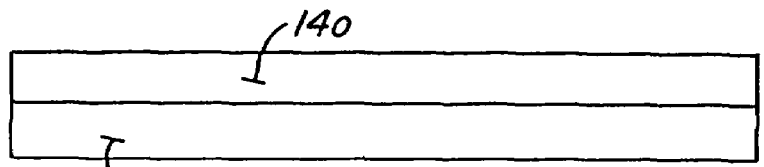
FIG. 2 shows a side view of the microdevice shown in FIG. 1 along the line 2-2.

The wall members 14a-14e, 14o, 14p are spaced so that each pair of adjacent wall members 14a-14e, 14o, 14p produces a fluid channel 16a-16d. For example, adjacent inner wall members 14a, 14b produce an inner fluid channel 16a. The inner wall members 14a, 14e and outer wall members 14o, 14p form outer fluid channels 16o, 16p. For example, inner wall member 14a and outer wall member 14p form a fluid channel 16p. FIG. 2 shows a side view of the outer wall member 14o and the substrate 12 of the microdevice 10. In this example, the outer wall member 14o is solid along its length and does not have an opening like the inner wall members 14a-14e.

The fluid channels 16a-d, 16o, 16p in the microdevice 10 shown in FIG. 1 are substantially parallel to each other. However, in other embodiments of the invention, the fluid channels and the wall members forming those fluid channels may have any suitable configuration. For example, the fluid channels in the microdevice may be fabricated so that they are perpendicular or non-linear. Moreover, while the microdevice 10 shown in FIG. 1 has six fluid channels, it is understood that in embodiments of the invention, the microdevice 10 may have any suitable number of fluid channels. For example, in some embodiments, the microdevice 10 may have more than 10, 20 or 50 fluid channels.

Each inner wall member 14a-14e can structurally discontinue at an intermediate region to form an opening 20a-20e. Although the embodiment shown in FIG. 1 has one opening 20a-20e per wall member 14a-14e, it is understood that embodiments of the invention are not limited to microdevices with one opening per wall member. For example, each wall member may have 2, 3, 4, or any suitable number of openings. Moreover, as will be explained in further detail below, in some embodiments, the wall members need not have any openings in them.

In some embodiments, the openings 20a-20e in the members 14a-14e may be aligned to form a slot 140. The slot 140 formed by the aligned openings 20a-20e can, for example, permit a probe (not shown) to pass from one fluid channel to another fluid channel without being removed from the microdevice 10. Illustratively, a probe (not shown) can detect a characteristic of a first fluid flowing in a first fluid channel 16a. After detecting the characteristic, the probe may move through the opening 20b and into a second fluid channel 16b. The probe may then detect a characteristic (e.g., pH, conductivity, fluorescence, and/or temperature) in a second fluid flowing in the second fluid channel 16b without removing the probe from the microdevice 10. Fluids in the other fluid channels 16c, 16d, 16o may be detected in a similar manner. The probe need not be withdrawn from the fluids flowing in the fluid channels 16a-16d, 16o, 16p and need not be exposed to the outside environment. By detecting the characteristics of fluids in this manner, detection occurs quickly and accurately.

Each inner wall member 14a-14e can include one or more pairs of opposing beveled structures 24a-24e that form openings 20a-20e in the respective wall members 14a-14e. By using beveled structures in a wall member, a fluid having a laminar profile flowing in a fluid channel formed by the wall member is more likely to retain its laminar profile at the opening formed by the beveled structures. The beveled structures 24a-24e may have any suitable geometry. For example, two examples of beveled structures 24a are shown in FIGS. 3(a), 3(b).

Figure 3A:
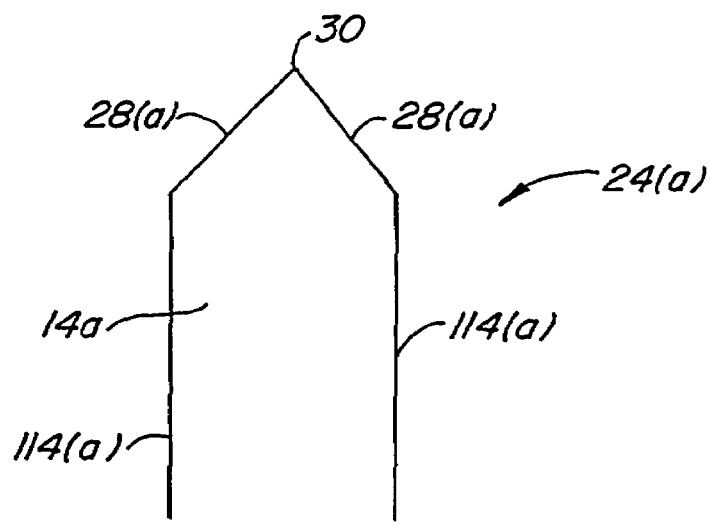
FIGS. 3(a)-3(c) show partial top views of portions of wall members with beveled ends.

In FIG. 3(a), a wall member 14a includes a beveled structure 24a. The beveled structure 24a includes a pair of tapering walls 28a. In this example, the tapering walls 28a are substantially straight. Also, the tapering walls 28a converge in an inward direction to an apex 30 and may form an angle with respect to substantially parallel side surfaces 114a of the wall member 14a. The angle may be, for example, from about 1 degree to about 89 degrees. In other embodiments, the angle may be, for example, about 2 to about 20 degrees.

Figure 3B:
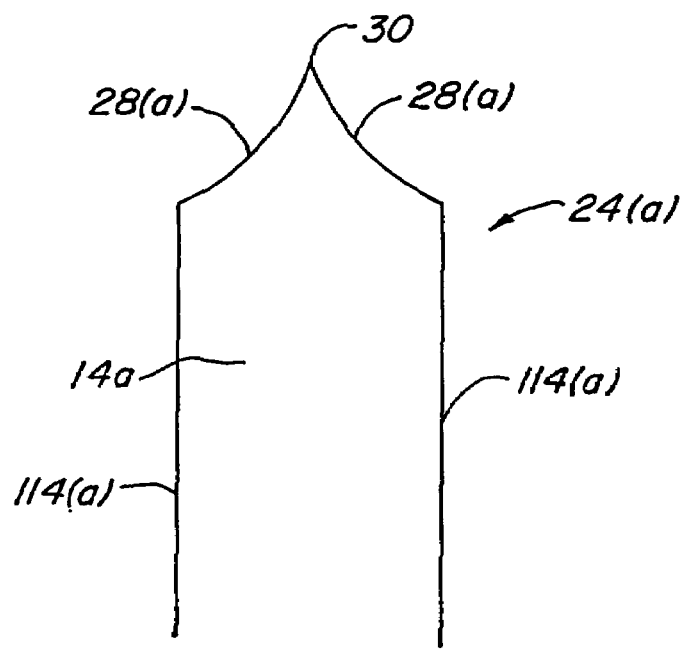
Figure 3C:
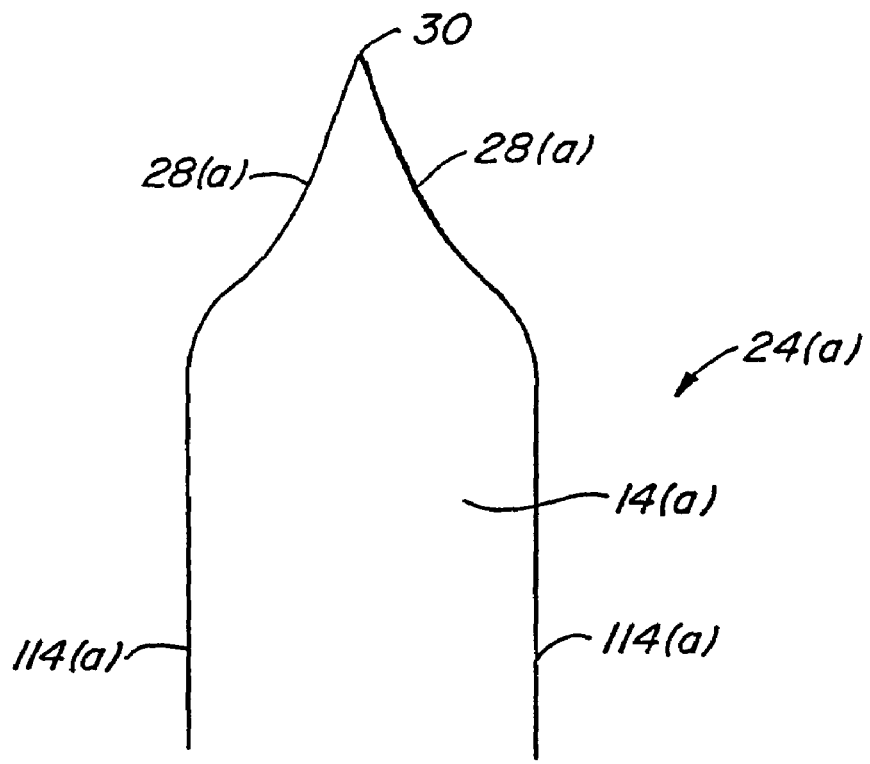

FIG. 3(b) shows another example of a beveled structure 24a of a wall member 14a. The beveled structure 24a also has a pair of tapering walls 28a that converge to an apex 30. However, unlike the embodiment shown in FIG. 3(a), the beveled structure shown in FIG. 3(b) has curved tapering walls 28a. In this example, the tapering walls 28(a) curve inwards towards the apex 30. The beveled structure 24a shown in FIG. 3(b) has a generally funnel-shaped appearance when viewed from the top. The beveled structure 24a shown in FIG. 3(c) is similar to the previously shown beveled structures, but includes a smooth transition between the side surfaces 114(a) and the tapering walls 28(a). As shown, side surfaces 114(a) may be substantially parallel to each other and may then gradually curve inwardly in the region of the tapering walls 28(a).

The particular geometries of the features of the microdevice 10 may vary. Examples of features include wall member thicknesses, fluid channel heights, and fluid channel widths. Typically, the features of the microdevice 10 have at least one dimension that is less than about 1000 microns. For example, in some embodiments, the width and depth of each fluid channel may be between about 10 microns and about 500 microns. In other embodiments, the width or depth of each fluid channel may be between about 50 microns and about 200 microns. In some embodiments, the fluid channels may sometimes be referred to as "microchannels".

Figure 4:
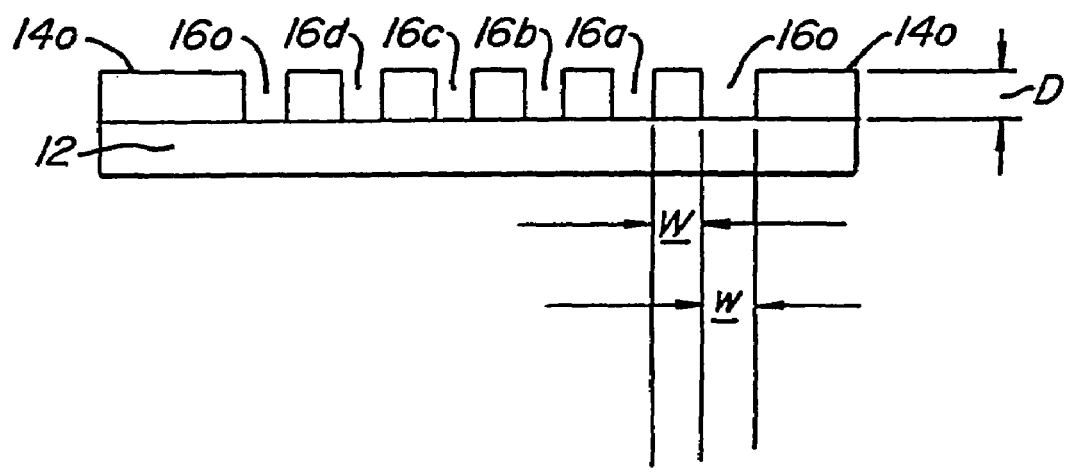
FIG. 4 shows an end cross-sectional view of the microdevice shown in FIG. 1 along the line 4-4.

Referring to FIG. 4, each wall member 14a-14e, 14o, 14p may have a width "W" of less than about 1 mm (e.g., about 20 microns to about 100 microns) and a height "D" of less than about 1 mm. In some embodiments, D may be from about 50 microns to about 500 microns (e.g., about 200 microns). Each fluid channel 16a-16d, 16o, 16p may have a width "w" of less than about 1 mm (e.g., about 50, 100, 150, or 200 microns).

Figure 5:
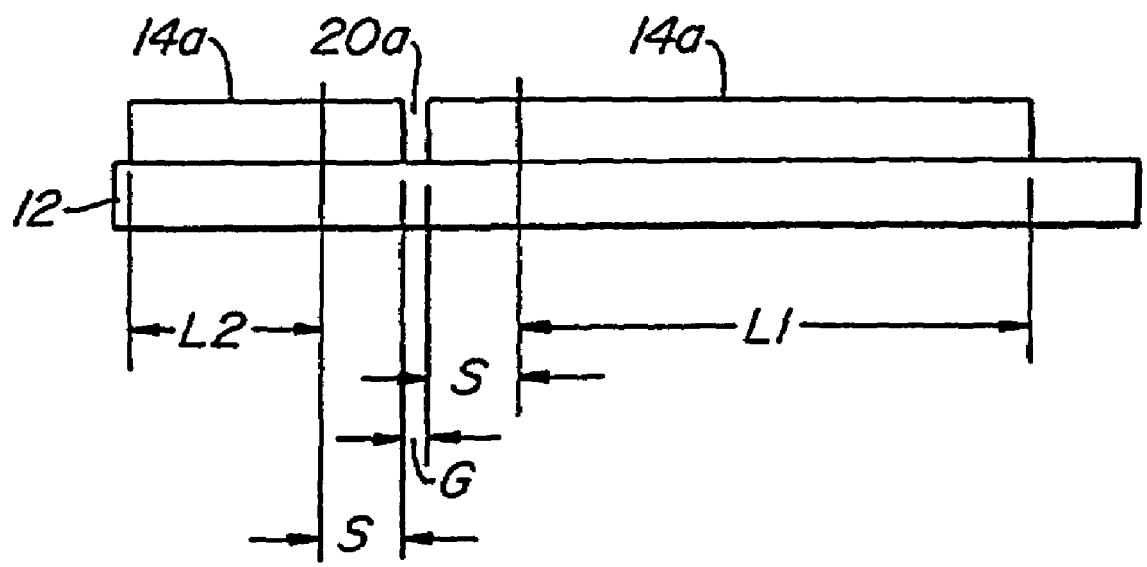
FIG. 5 is a cross-sectional view of the microdevice shown in FIG. 1 along the line 5-5.

Referring to FIG. 5, the distance "G" of each opening 20a formed in a wall member 14a may be about 1 mm or less. For example, in some embodiments, G may be from about 50 microns to about 400 microns (e.g., about 200 microns). As shown in FIG. 5, the wall member 14a structurally discontinues to form an opening 20a so that the wall member 14a has two distinct, separated portions. Each portion of the wall member 14a may have two parts. One part may have substantially parallel sidewalls and may have a length "L1" or "L2". The other part may be a beveled structure that extends along the length of the wall member 14a distance "S". Typically, the distance L1 or L2 is much greater than the length S. For example, the distance L1 or L2 may be about 1 cm or more (e.g., about 1 cm to about 5 cm). The length S may be about 50 microns to about 750 microns. Of course, the dimensions of the elements of the microdevice 10 may have values that are more or less than the specifically mentioned values.

Again referring to FIG. 1, the fluid channels 16a-16d, 16o, 16p may have any suitable length or configuration. The length of each fluid channel 16a-16d, 16o, 16p may be from about 1 to about 20 mm in length, or more. For example, the length of each fluid channel 16a-16d, 16o, 16p can be from about 2 to about 8 mm. The distance between the corresponding points (e.g., opposing apexes) of opposed beveled structures in a wall member may be between about 50 and about 500 microns in some embodiments. Any channel cross-section geometry (trapezoidal, rectangular, v-shaped, semicircular, etc.) can be employed in the microdevice 10. Trapezoidal or rectangular cross-section geometries may be used in the fluid channels 16a-16d, 16o, 16p. Such geometries may be used with standard fluorescent detection methods.

Fluids such as liquids or gases may be supplied to the microdevice 10 in any suitable manner. For example, bulk-loading dispensing devices can be used to load all fluid channels 16a-16d, 16o, 16p of the microdevice 10 at once with the same or different fluids. Alternatively, integrated or non-integrated microcapillary dispensing devices may be used to load fluids separately into each fluid channel 16a-16d, 16o, 16p of the microdevice 10.

The flow of the fluids within the fluid channels 16a-16d, 16o, 16p can be controlled by the selective application of voltage, current, or electrical power to the substrate to induce and/or control the electrokinetic flow of the fluids. Alternatively or additionally, fluid flow may be induced mechanically through the application of, for example, differential pressure or acoustic energy to a fluid. Such fluid flow control mechanisms are used in microfluidic devices and are known in the art.

As noted, each of the fluids flowing in the fluid channels 16a-16d, 16o, 16p may have a laminar profile. In this regard, the Reynolds number, Re, for the fluid streams in the fluid channels 16a-16d, 16o, 16p may be greater than 0 to less than or equal to about 2300. Preferably, Re is from about 100 to about 2000. Re may be defined as follows:

$$Re = \frac{\rho V_{ave} D_h}{\mu}$$

$\rho$ is the density in gm/cm$^3$, $\mu$ is viscosity in gm/cm·sec, $V_{ave}$ is the average velocity of the fluid, and $D_h$ is the hydraulic diameter. The hydraulic diameter, $D_h$, may be defined as follows:

$$D_h \text{ (cm)} = \frac{4 \times \text{Cross-Section Area (cm}^2)}{\text{Wetted Perimeter (cm)}}$$

Although the fluids in the channels preferably have a laminar profile, adjacent fluids flowing in adjacent fluid channels may slightly intermingle (e.g., by diffusion) via the opening that communicates the adjacent fluid channels. However, the degree of intermingling between fluids in adjacent fluid channels does not typically interfere with any measurements or detections made by a probe.

Although many of the previously described examples have different sample fluids flowing through the fluid channels 16a-16d, 16o, 16p in the microdevice 10, in other embodiments of the invention, non-sample fluids such as wash fluids may be included in one or more of the fluid channels 16a-16d, 16o, 16p. For example, a wash fluid that can be used to wash a probe may flow through one or more fluid channels 16a-16d, 16o, 16p. For example, a fluid channel 16c containing a wash solution is disposed between two fluid channels 16b, 16d containing sample fluids. A probe (not shown) may be inserted into the fluid channel 16b to detect a characteristic of a sample fluid flowing in the fluid channel 16b. To detect a characteristic, the probe may be, for example, positioned in fluid channel 16b between the openings 20b, 20c or may be upstream or downstream of the point between the openings 20b, 20c. After detecting the characteristic, the probe may pass through the opening 20c in the wall member 14c to the fluid channel 16c containing a wash fluid. In the fluid channel 16c, the wash fluid removes any materials that may be disposed on the probe and that may impede the probe's ability to detect a characteristic in a different fluid. After the probe is washed, the washed probe may pass through the opening 20d in the wall member 14d to the other fluid channel 16d containing the other sample fluid. The washed probe can then detect a characteristic of the sample fluid in the fluid channel 16d. Alternatively or additionally, one or more of the fluid channels 16a-16d, 16o, 16p may contain a calibration fluid that can be used to calibrate, for example, a probe. The probe can be calibrated while being disposed in a calibrating fluid and may move to a fluid channel with a sample fluid after the probe is calibrated.

Figure 6:
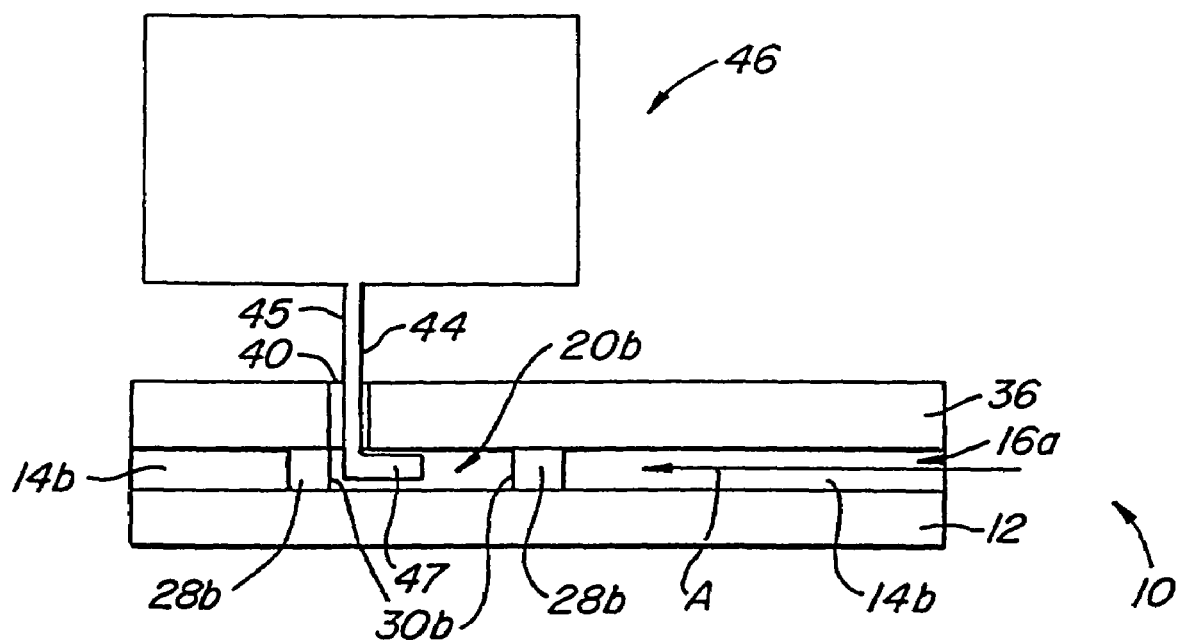
FIG. 6 is a side cross-sectional view of an analytical system shown in FIG. 7 along the line 6-6.

FIG. 6 shows an analytical assembly comprising a probe assembly 46 and a microdevice 10. The microdevice 10 in FIG. 6 is similar to the previously described microdevice 10 shown in FIG. 1, except that the microdevice 10 shown in FIG. 6 includes a cover 36. The cover 36 may also comprise a plurality of fluid inlets (not shown) and a plurality of fluid outlets (not shown) that provide fluids to and remove fluids from the fluid channels 16a-16d, 16o, 16p in the microdevice 10.

The cover 36 is supported by the pair of outer wall members 14o, 14p and may include a slot 40. A pair of opposed, generally parallel, boundaries may define the slot 40 in the cover 36. When the cover 36 is disposed on the wall members, the slot 40 in the cover 36 is aligned with and disposed over the slot 140 formed by the holes 20a-20e in the inner wall members 14a-14e (see FIG. 1). The boundaries defining the slot 40 in the cover 36 may or may not be generally aligned with apexes of the beveled structures in the wall members 14a-14e. A probe 44 of a probe assembly 46 is inserted through the slot 40 in the cover 36 so that an end portion 47 of the probe 44 is disposed in a fluid channel 16a and in the slot 140 in microdevice 10.

In the analytical assembly shown in FIG. 6, the probe 44 may include an intermediate portion 45 that is upright and an end portion 47 that is skewed with respect to the intermediate portion 45. The end portion 47 of the probe 40 may be substantially perpendicular to the intermediate portion 45. In other embodiments, the end portion of the probe need not be perpendicular to an intermediate portion of the probe. For example, in some embodiments, the end portion of a probe may be co-linear with an intermediate portion of the probe.

In this example, the end portion 47 of the probe 44, is directed towards the upstream direction of the fluid flowing (which flows in direction A) through the fluid channel 16a. As the fluid flows through the fluid channel 16a, the end portion 47 of the probe 44 may receive some of the fluid flowing in the fluid channel 16a. Once the fluid is received, the end portion 47 may remove a portion of the fluid for sampling. For example, the probe 44 associated with the probe assembly 46 may include a micro-pipe that collects some of the fluid flowing through the fluid channel 16a. Once collected, the sample may then be transferred to a mass spectrometer, HPLC (high pressure liquid chromatography) apparatus, or a gas chromatography apparatus. In some embodiments, the micro-pipe could also be used to introduce a fluid into a fluid channel. The introduced fluid can be added to a fluid channel without disturbing the laminar flow profile in the flowing fluid. Other suitable detection assemblies, detection devices, and analytical systems according to embodiments of the invention are described in further detail below.

Figure 7:
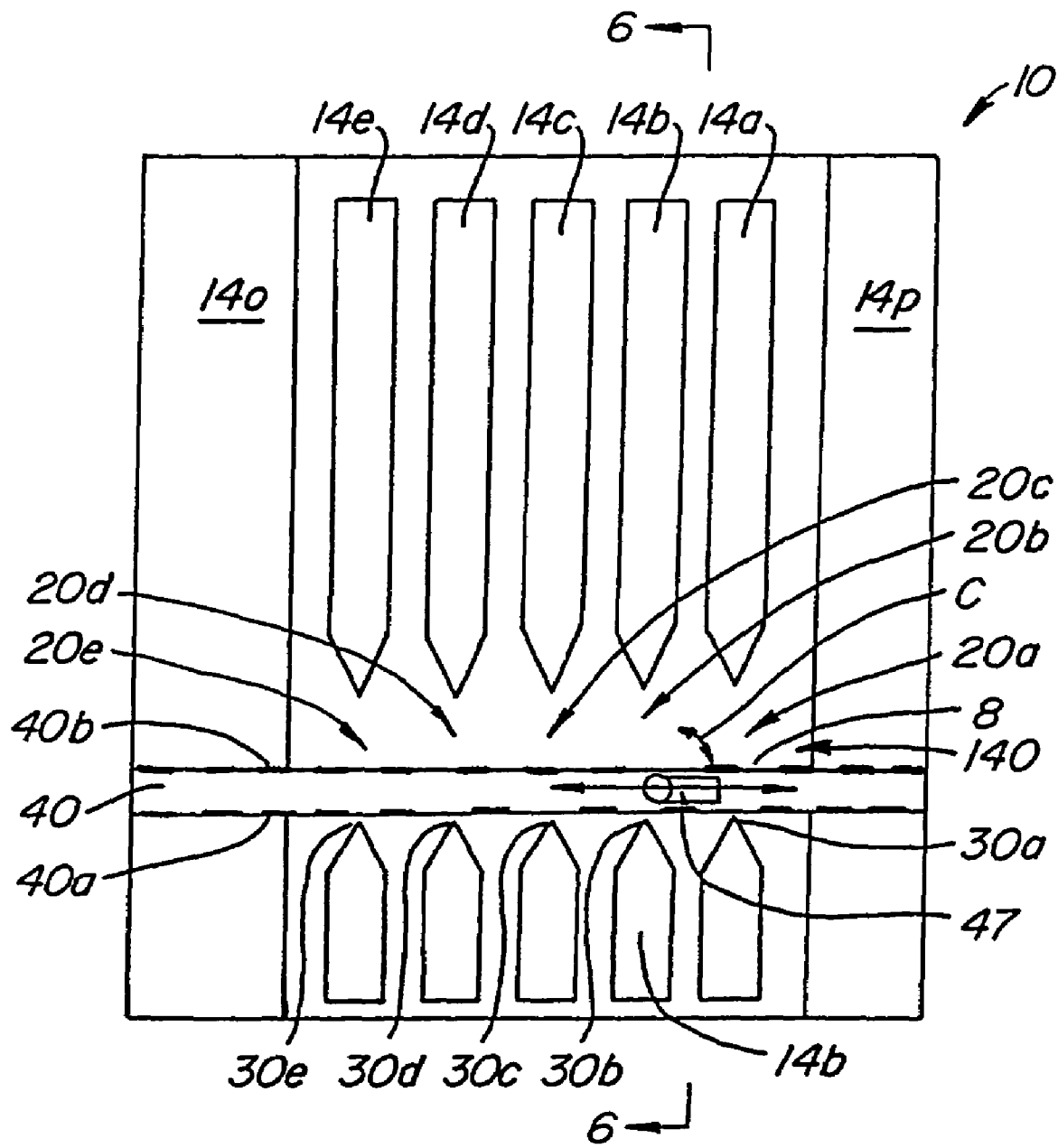
FIG. 7 is a top cross-sectional view of some components of an analytical assembly according to an embodiment of the invention. Boundaries forming a slot in a cover are shown by dotted lines.

Referring to FIGS. 6 and 7, to move the probe 44 from fluid channel to fluid channel, the probe 44 may move in the desired direction in the slot 40, such as in direction of arrow B (see FIG. 7). Because the end portion 47 in this example protrudes from the upright portion 45 of the probe 44, in order to pass the end portion 47 through the slot 40, the end portion 47 may be initially aligned with the slot 40 and may then be inserted through the slot 40 in the cover (not shown in FIG. 7). Once the end portion 47 is in the slot 140 formed by the openings 20a-20e in the wall members 14a-14e, it is rotated about 90° in direction of the arrow C shown in FIG. 7 so that the end portion 47 is directed toward the flowing fluid in the fluid channel in which it is disposed. The boundary 40a at slot 40 may be aligned with the apexes 30a-30e of the wall members 14a-14e so that the end portion 47 of the probe 40 does not contact the apexes 30a-30e as the probe 44 is inserted into the slot 40.

Figure 8:
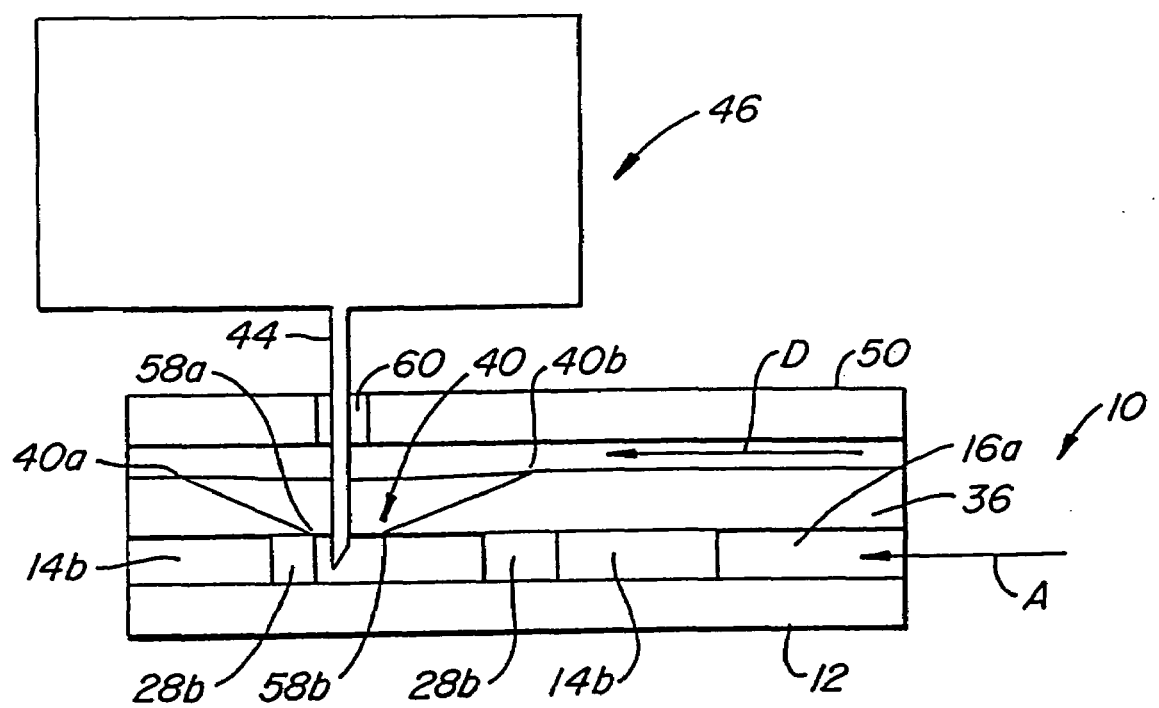
FIG. 8 is a side cross-sectional view of an analytical assembly according to an embodiment of the invention.

FIG. 8 shows another analytical assembly embodiment of the invention. In this embodiment, the microdevice 10 includes a cover 36 having slot 40. A lid 50 is on the cover 36 and is spaced from the cover 36 by supports (not shown). The slot 40 in the cover 36 is defined by downwardly sloping planar surfaces from boundaries 40a and 40b that terminate in edges 58a and 58b, respectively. The lid 50 also has a slot 60 that is generally aligned with the slot 40 in the cover 36. The probe 44 may pass through both the slot 60 in the lid 50 and the slot 40 in the cover 36.

The embodiment shown in FIG. 8 can be used when the fluids flowing through the fluid channels are gases. As gases flow through the fluid channels defined by the wall members and the substrate, another gas such as an inert gas (e.g., a noble gas, nitrogen, etc.) flows between the lid 50 and cover 36. The inert gas may flow in a direction of the arrow D and may have a higher pressure than the gases flowing through the fluid channels formed by the wall members on the substrate 12. The higher pressure gas flowing between the lid 50 and the cover 36 confines gases flowing in the fluid channels between the cover 36 and the substrate 12 and prevents diffusion of the same out of the fluid channels and into the zone between the lid 50 and the cover 36. In the embodiment shown in FIG. 8, the probe assembly 46 has a probe 44 with a beveled end and not a protruding end portion as in the previous examples. The probe assembly in the embodiment shown in FIG. 8 could also have a protruding end portion if desired.

Figure 9:
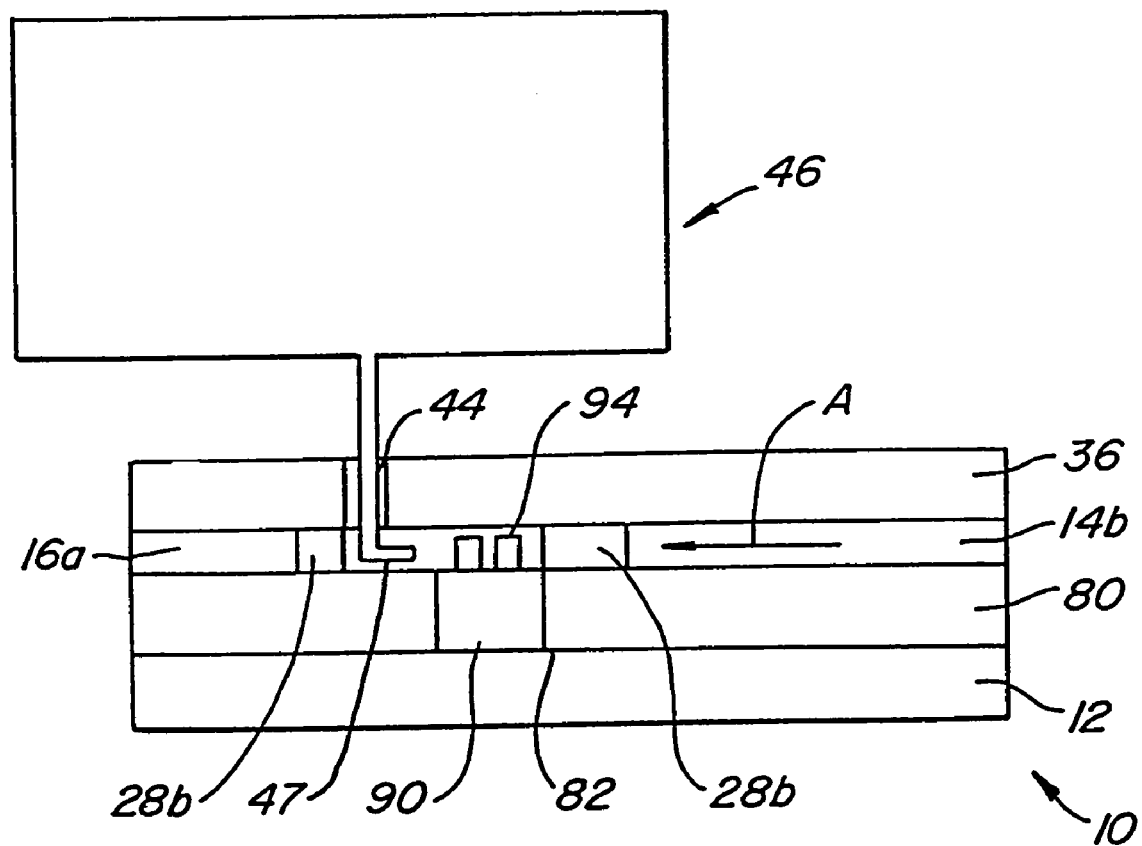
FIG. 9 is a side cross-sectional view of an analytical assembly according to an embodiment of the invention.
Figure 10:
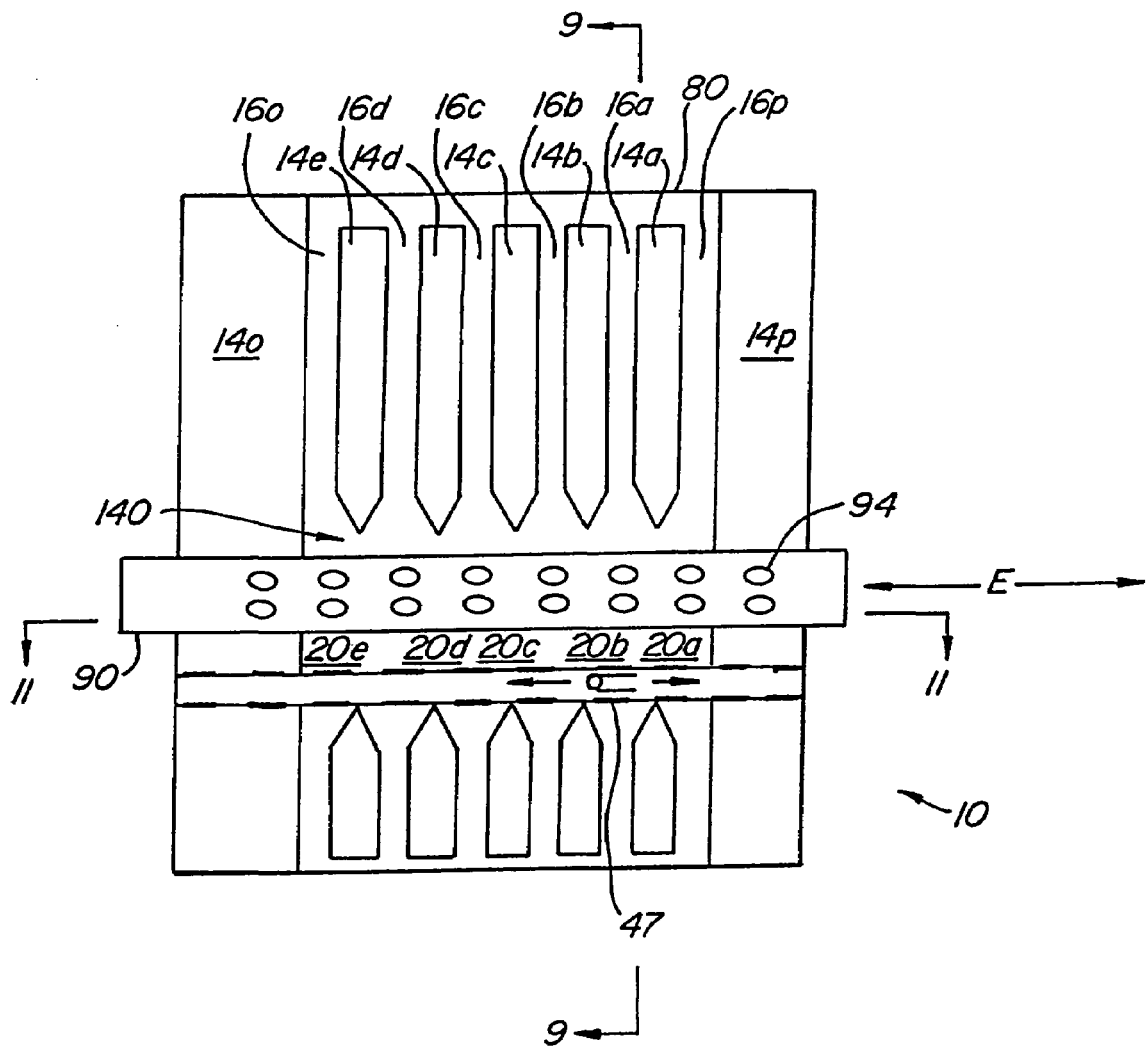
FIG. 10 is a top cross-sectional view showing some components of an analytical assembly according to an embodiment of the invention.
Figure 11:
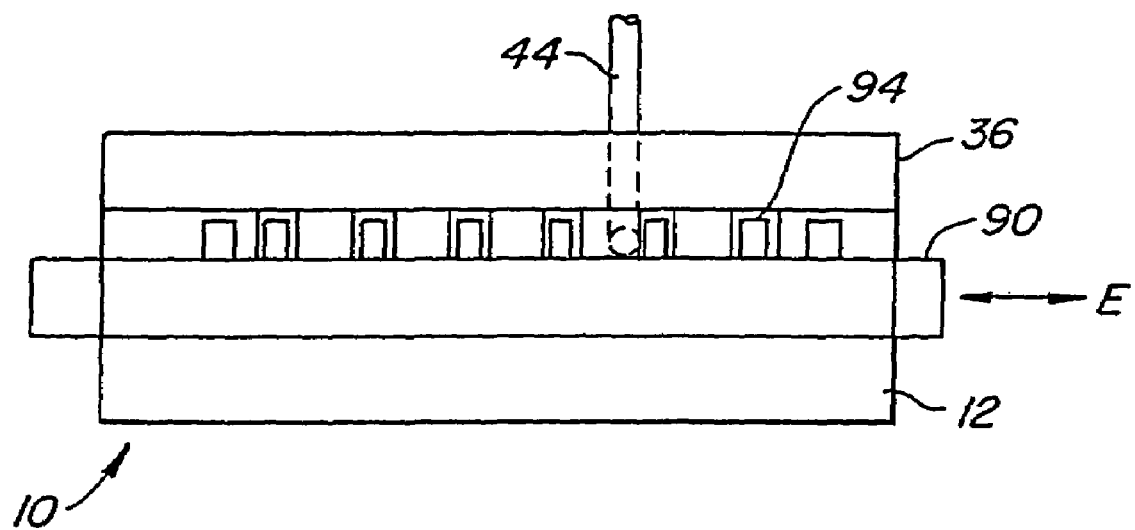
FIG. 11 is an end cross-sectional view of an analytical assembly shown in FIG. 10 along the lines 11-11. Invisible lines show boundaries of a slot in a cover.

FIG. 9 shows another analytical assembly embodiment of the invention. The microdevice 10 in this embodiment has a substrate 12, a bottom member 80, a slide member 90, a cover 36, and a probe assembly 46, and a probe 44. The bottom member 80 has a passage 82 where the slide member 90 is disposed. The slide member 90 may slide in a direction transverse to the orientation of the fluid channels 16a-16e, 16o, 16p (i.e., in direction of the arrow E in FIGS. 10 and 11). As shown in FIGS. 10 and 11, the substances 94 disposed on the slide member 90 may be aligned with the fluid channels 16a-16e, 16o, 16p so that the fluids flowing within the fluid channels 16a-16e, 16o, 16p come in contact with the substances 94.

Illustratively, with reference to FIG. 9, the slide member 90 may support substances 94 that can contact a fluid flowing through the fluid channel 16a prior to reaching the probe 44 of the probe assembly 46. The characteristic of the fluid in the fluid channel 16a can be detected after the fluid has contacted the substances 94 on the slide member 90. For example, the substances 94 may comprise antibodies for capturing molecules contained in the fluid flowing in the fluid channel 16a. The probe 44 may then contact the downstream fluid and the probe 44 can detect a characteristic of the downstream fluid. The concentration of the molecules in the fluid can then be determined. If the concentration of the molecules upstream of the slide member 90 is greater than the concentration of the molecules downstream of the slide member 90, then it can be concluded that the substances 94 on the slide member 90 interact with the molecules in the fluid.

In some embodiments, the microdevice 10 can be used to deposit successive layers of material on a slide member 90. This may be done by pulling the slide member 90 through the passage 82 in the microdevice 10. The slide member 90 may be exposed to a succession of many different fluids that may deposit different materials on the slide member 90.

II. Detection Assemblies and Analytical Systems

The detection methods, detection assemblies, and analytical systems used in embodiments of the invention are not limited to those described above, and may employ any suitable optical, electrical, physical, and/or chemical detection techniques. Radiation such as visible, infrared, or ultraviolet radiation from the fluids may be detected by a detection assembly being an optical detection assembly.

In many of the embodiments described above, detection assemblies and analytical systems using probes that comprise micropipes are described in detail. However, embodiments of the invention are not limited to the use of such micropipes. For example, the end portion of a probe may contact the fluid flowing in a fluid channel to detect a particular characteristic of the fluid, without collecting a sample of the fluid. The probe may be coupled to signal analyzer (such as that sold by Hewlett-Packard, for example), an oscilloscope (such as that sold by Tektronix or Hewlett-Packard), or a lock-in amplifier (such as that commercially employed by Stanford Research System or. EG&G).

The probe may comprise a physical sensor, a biological sensor, a chemical sensor, or an electrical sensor. Examples of physical sensors include thermocouples, pressure sensors, flow sensors, optical fibers, etc. Examples of biological sensors include sensors with immobilized enzymes or immunoassays. Examples of electrical or chemical sensors include sensors with interdigitated electrodes having optional polymer coatings, atomic force microscopes (AFMs), Ion Sensitive Field Effect Transistors (ISFETs), light addressable potentiometric sensors (LAPSs), pH meters, and scanning probe potentiometers (SPPs). These and other types of sensors are described in Manalis et al, *Applied Physics Letters*, Volume 76, No. 8, Feb. 21, 2000, and other references. In comparison to optical detection devices, chemical sensors and electrical sensors are desirable as they do not need to use more expensive and inconvenient fluorescent or radiochemical tagging processes.

An atomic force microscope allows high force sensitivity mapping of biological cells and molecules such as DNA and proteins. The AFM can obtain stable images of individual biomolecules while operating in physiological environments. In an AFM, unlike optical detection devices, molecules can be imaged directly, and the dimensions of the probe can determine the spatial resolution.

Field effect devices such as the ISFET and the LAPS can directly detect molecular and ionic charge. For example, the LAPS device has been used in a microphysiometer to monitor the response of cells to chemical substances by measuring the rate of change of the pH as protons are excreted from cells during metabolism. LAPS devices may be commercially obtained from Molecular Devices of Sunnyvale, Calif.

Preferably, the active areas of electrical detection devices such as AFMs, ISFETs, and SPPs are small. In some embodiments, the active area in such detection devices is less than about a square millimeter, or less than 100 square microns. When the active area is small, the detection sensitivity and resolution is improved in comparison to detection devices with larger active areas.

Figure 12:
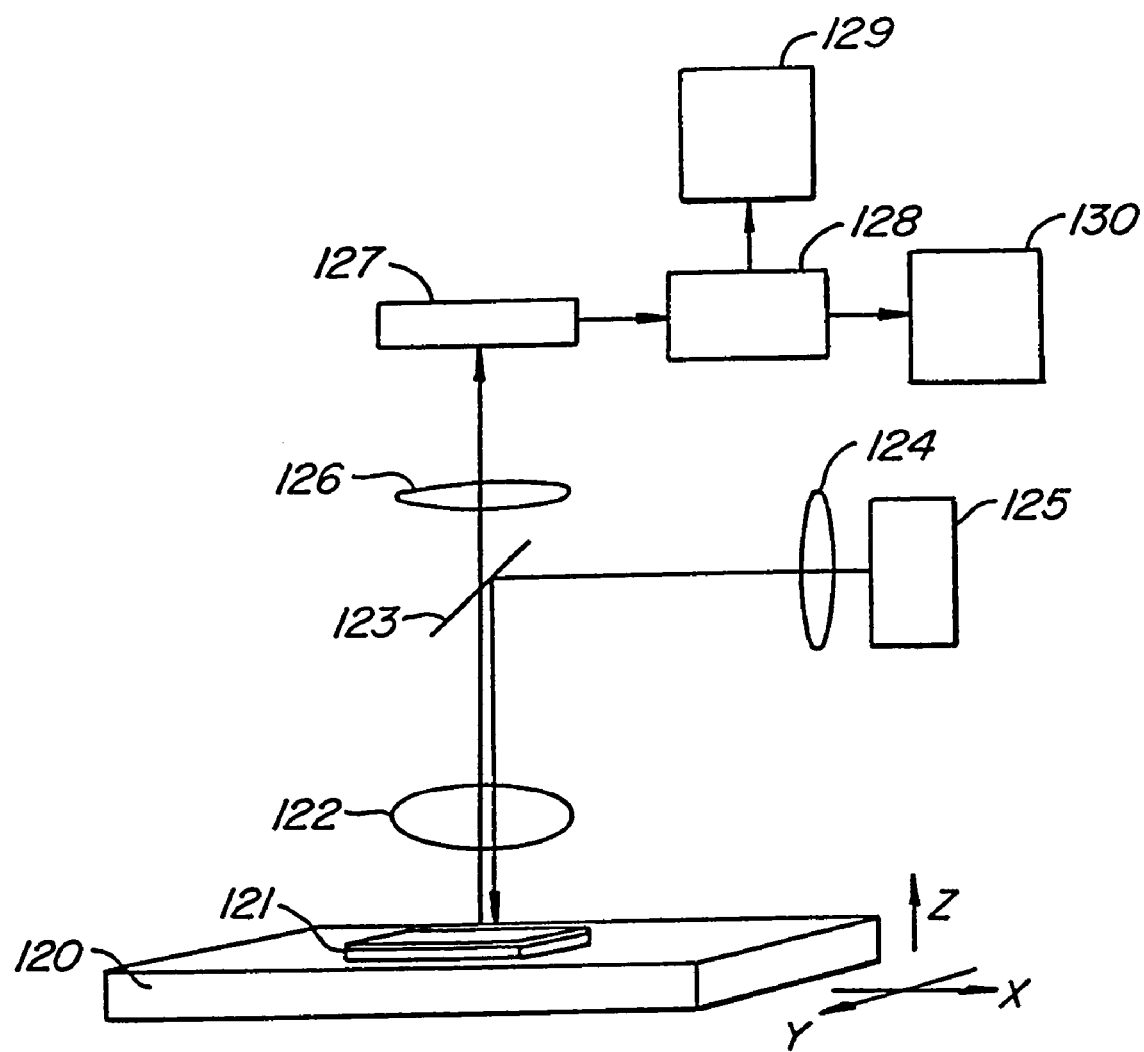
FIG. 12 is a schematic diagram of an analytical assembly embodiment.

Other detection devices may be used instead of or in addition to one or more probes. In some embodiments, detection devices such as one or more optical detection devices may be used to detect the characteristics of fluids flowing in the fluid channels in a microdevice. For example, FIG. 12 shows a schematic diagram of an analytical assembly comprising a detection assembly that detects fluorescent light coming from the fluids on a microdevice. In the illustrated detection assembly, the microdevice 121 is positioned on a base plate 120. Light from a 100 W mercury arc lamp 125 is directed though an excitation filter 124 and onto a beam splitter 123. The light is then directed through a lens 122, such as a Micro Nikkor 55 mm 1:2:8 lens and onto the fluids flowing in the fluid channels of the microdevice 110. Fluorescence emission from the device returns through the lens 122 and the beam splitter 123. After also passing though an emission filter 126, the emission is received by a cooled CCD camera 127, such as the Slowscan TE/CCD-10245F&SB (Princeton Instruments). The camera 122 is operably connected to a CPU 128, which is, in turn, operably connected to a VCR 129 and monitor 130.

In some embodiments of the invention, the analytical assembly may comprise a detection assembly comprising a plurality of detection devices and a microdevice. The microdevice may comprise a plurality of wall members and a plurality of fluid channels, wherein each of the fluid channels is defined by adjacent wall members in the plurality of wall members. The analytical assembly may be used to detect characteristics of different fluids flowing in different fluid channels substantially simultaneously. In these embodiments, the wall members of the microdevice may or may not have openings that allow adjacent fluid channels to communicate with each other. By using multiple detection devices, the characteristics of fluid flowing in the fluid channels of a microdevice may be detected in parallel, thus increasing the speed of detection and analysis.

In one example, a plurality of different biological moieties can be screened in parallel for their ability to interact with a component of a fluid sample. A fluid sample can be delivered to the reactive sites in fluid channels in a microdevice where each of the different biological moieties is immobilized on a different site of the microdevice. Then, characteristics of the fluids passing downstream of the reactive sites may be detected substantially in parallel with a plurality of detection devices to study the interaction of the component with the immobilized biological moieties at each reactive site.

Figure 13:
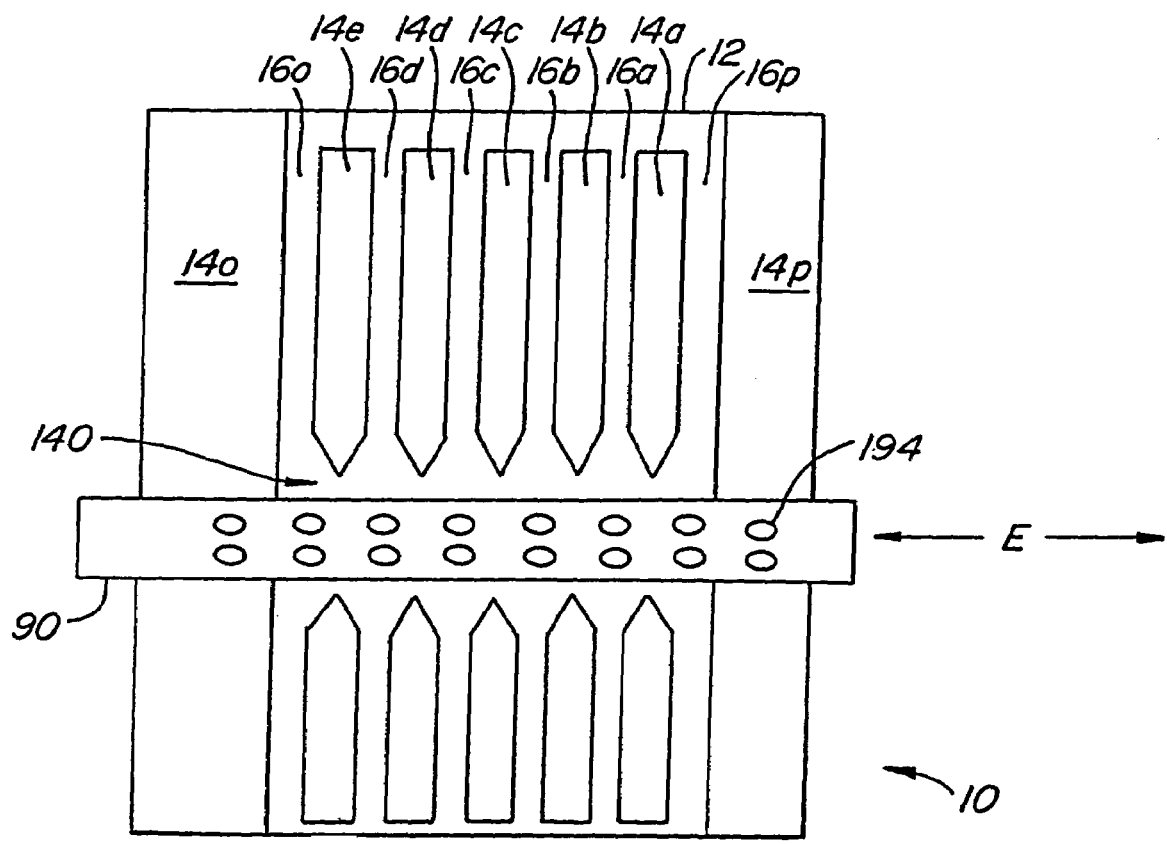
FIG. 13 is a top view of an analytical assembly according to an embodiment of the invention.

Illustratively, referring to FIG. 13, a slide member 90 may comprise a number of detection devices such as sensors 194 and may form a detection assembly. The sensors 194 on the slide member 90 may contact the fluids flowing in the fluid channels 16a-16e, 16o, 16p and may subsequently detect characteristics of the fluids. The sensors 194 may be, for example, conductivity sensors, biosensors, temperature sensors, etc. In these embodiments, a probe assembly with an elongated probe, and a cover with a slot for the elongated probe are not needed.

Other detection assemblies with multiple detection devices may be used in embodiments of the invention. For example, probe assemblies like the probe assembly 46 shown in FIG. 6 can be used. The probe assembly, however, may comprise two or more elongated probes 44. These probes may be spaced so that they can be inserted into plural fluid channels simultaneously to detect characteristics of the fluids flowing in these fluid channels substantially simultaneously. In some embodiments, the number of probes in the detection assembly may be equal to or less than the number of fluid channels in the microdevice. For example, if a microdevice has six fluid channels, a probe assembly with six probes that are insertable within the six fluid channels can be used to substantially simultaneously detect characteristics of the six fluids flowing in the six fluid channels.

In another example, a plurality of optical detectors may be positioned to receive optical signals coming from a plurality of fluids flowing in their respective fluid channels on a microdevice. For example, the plurality of optical detectors may comprise a charge coupled device (CCD) array or a photodiode array. These arrays may be positioned to receive optical signals coming from the fluids flowing in the fluid channels. In some embodiments, radiolabels or fluorescent tags on molecules in fluids flowing in the fluid channels in a microdevice may provide such optical signals.

III. Exemplary Methods of Manufacture

The microdevices according to embodiments of the invention may be made according to any suitable process. For example, in some embodiments, portions of a body of material may be removed to form a plurality of wall members. In these embodiments, the wall members may be integrally formed with the substrate. Examples of suitable material removal processes include bulk micromachining, sacrificial micromachining, focused ion-beam milling, electrostatic discharge machining, ultrasonic drilling, laser ablation, mechanical milling and thermal molding techniques. Conventional photolithographic and etching processes may be used to etch a body to form a plurality of wall members and fluid channels in the body. Etching processes such as reactive ion etching (RIE) or deep reactive ion etching (DRIE), or wet etching may be used to etch an appropriate body of material. In some embodiments, the wall members and the underlying substrate may be formed by molding. In other embodiments, wall members may be formed on a substrate. For example, wall members may be formed on or bonded to a body to form a plurality of fluid channels. For example, wall members may be formed by electroplating (e.g., high aspect ratio plating).

If desired, after the fluid channels are formed in the microdevice, the surfaces defining the fluid channels may be coated with a material. The material coated on the walls or bottom surfaces defining the channels may be an adhesion layer, coupling agents, or substances that may potentially interact with fluids flowing through the fluid channels.

Any suitable material may be used as to form the substrate and the wall members in the microdevice. The materials used may be organic or inorganic, and may be transparent, translucent, or non-transparent. Materials that can be micromachined or microfabricated are preferred. Suitable micromachinable materials include silicon, glass, plastic and the like. Other suitable materials, and processes for forming a plurality of fluid channels in a microdevice may be found in U.S. patent application Ser. No. 09/115,397, which is assigned to the same assignee as the present application, and International Application No. PCT/US99/15968. Both of these applications are herein incorporated by reference in their entirety for all purposes.

EXAMPLE

A microdevice having ten fluid channels was fabricated by forming nine wall members in a silicon substrate. The wall members were formed in a silicon substrate using a deep reactive ion etch. Each of the wall members had an opening and the openings in the wall members were aligned to form a slot that passed across the nine wall members. The height of the wall members and the corresponding channel depth was about 200 microns. The width of each of the fluid channels was 110 microns, and the channel pitch was about 150 microns.

Buffered solutions with pH values of 4, 7, and 10 were fed to the different fluid channels in the microdevice. Because the fluid channel volumes were low, the Reynolds number for the solutions in the fluid channels was sufficiently low to maintain laminar flow at reasonable flow rates. With laminar flow, the solutions flowing in the ten fluid channels did not mix in the slot region of the microdevice. The flow rates for the solutions in the fluid channels were set for a maximum value of 500 nanoliters/minute.

The pH values of the different fluids flowing in the ten fluid channels were measured using a scanning probe potentiometer (SPP). The SPP had a probe was insertable into a fluid channel and had a sensitivity of less than 0.01 pH units and a spatial resolution of 10 microns.

The pH of the ten fluids flowing in the ten fluid channels was profiled by measuring the pH in a fluid channel proximate one side of the microdevice. After the pH values in this fluid channel are measured, the probe moves through the slot to the next adjacent fluid channel without removing the pH sensitive area of the probe from the flowing fluids. The pH value of the adjacent fluid channel was then measured. The pH values of the fluids in the remaining eight fluid channels were measured in a similar manner. The travel time between the fluid channels was about 1 second. The measurement time was about 5 seconds per channel.

Figure 14:
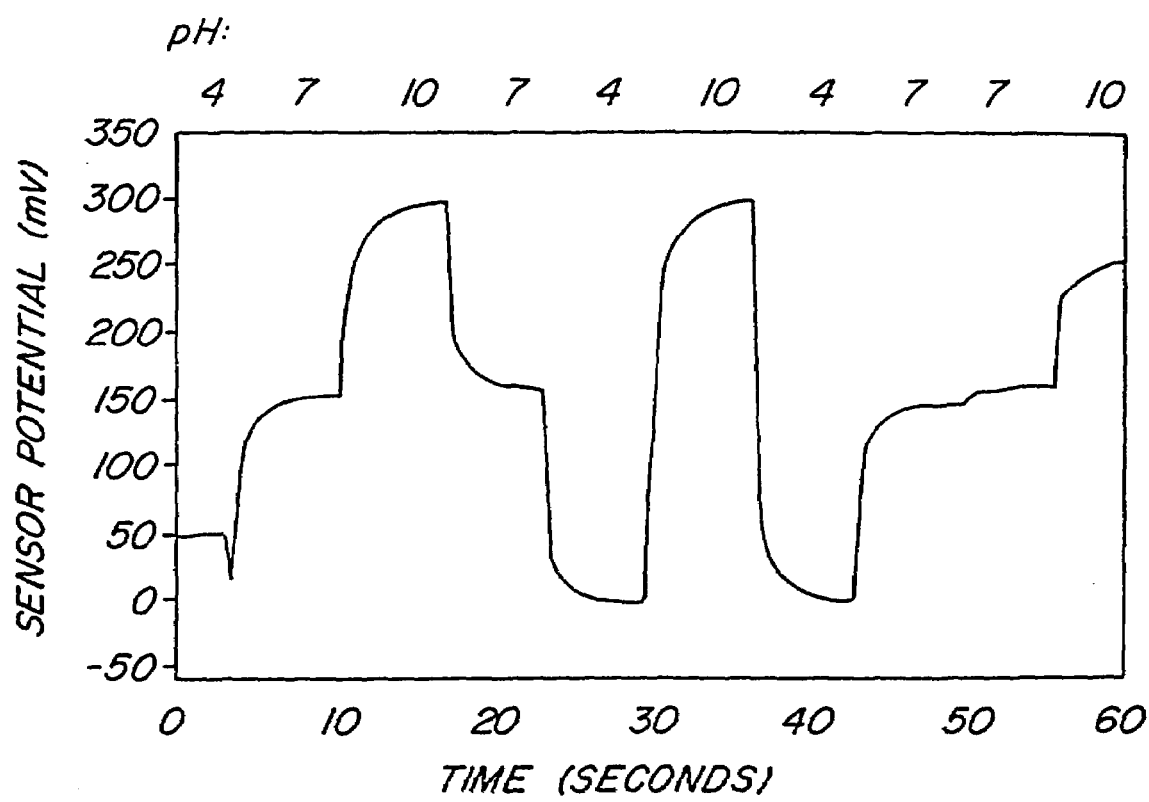
FIG. 14 is a graph of surface potential vs. time as a probe scans fluids flowing in fluid channels in a microdevice according to an embodiment of an invention.

A plot of sensor potential versus time during the scanning process is shown in FIG. 14. The relative potential difference between each fluid channel correlates closely to the actual pH values of the fluids in the channels (listed above the plot), except for the first and last edge channels. Each of the plateaus in the plot corresponds to a pH measurement of a fluid in a fluid channel. As shown in the plot, the time used to measure the pH values of the ten fluids in the ten fluid channels was less than one minute.

All patents, patent applications, and publications mentioned above are herein incorporated by reference in their entirety. The citation of such documents is not an admission such patents, patent applications, and publications are prior art.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, any feature of the embodiments using multiple detection devices may be used with any feature of the embodiments using wall members with openings without departing from the scope of the invention.

What is claimed is:

1. A microdevice for supporting a flowing fluid, the microdevice comprising:
   a substrate; and
   a pair of generally parallel, spaced wall members on the substrate, wherein at least one of the wall members includes a pair of structures defining an opening; and
   a slide member, wherein the slide member is disposed on the substrate and is adapted to slide through the opening.

2. The microdevice of claim 1 wherein the pair of structures are beveled structures.

3. The microdevice of claim 1 wherein the pair of structures are beveled structures, and wherein each of the beveled structures comprises a pair of inwardly tapering wall surfaces terminating in an apex.

4. The microdevice of claim 3 wherein each of the tapering wall surfaces form an angle of about 2 degrees to about 20 degrees with respect to a side surface of an intermediate portion of the wall member.

5. The microdevice of claim 3 wherein each tapering wall surfaces is curved.

6. The microdevice of claim 1 wherein a distance between the pair of structures is about 50 microns to about 400 microns.

7. The microdevice of claim 1 comprising three or more generally parallel wall members on the substrate.

8. The microdevice of claim 1 wherein the spaced wall members define a fluid channel that contains a fluid with a laminar flow profile.

9. The microdevice of claim 1 further comprising a cover disposed on the wall members.

10. The microdevice of claim 1 wherein each of the wall members include an opening, and wherein the openings in the respective wall members are substantially aligned to form a slot.

11. An analytical assembly comprising:
    the microdevice of claim 1; and
    a probe having an end portion that is insertable between the spaced wall members.

12. A microdevice comprising:
    a substrate;
    a plurality of wall members; and
    a plurality of fluid channels, wherein each of the fluid channels is defined by adjacent wall members in the plurality of wall members, wherein each wall member comprises an opening that is formed by opposed beveled structures of the wall member and that communicates the adjacent fluid channels.

13. The microdevice of claim 12 wherein the openings in the respective wall members are substantially aligned to form a slot.

14. The microdevice of claim 12 wherein the openings in each of the wall members are structured to permit fluids having a laminar profile flowing on opposite sides of respective wall members from intermixing.

15. The microdevice of claim 12 further comprising a cover on the wall members and a lid spaced from the cover.

16. An analytical assembly comprising:
    a detection assembly comprising a plurality of detection devices; and
    a microdevice according to claim 12.

17. The analytical assembly of claim 16 wherein the plurality of detection devices comprise a plurality of probes.

18. The analytical assembly of claim 16 wherein the plurality of detection devices comprise a plurality of optical detectors.

19. The analytical assembly of claim 16 wherein the detection devices are disposed in the fluid channels in the microdevice.

* * * * *